United States Patent
Schmidt et al.

(10) Patent No.: US 12,269,840 B2
(45) Date of Patent: Apr. 8, 2025

(54) PROCESS FOR THE PREPARATION OF A CYCLIC DINUCLEOTIDE

(71) Applicant: Bristol-Myers Squibb Company, Princeton, NJ (US)

(72) Inventors: Michael Anthony Schmidt, Cranbury, NJ (US); Bin Zheng, Kendall Park, NJ (US); Benjamin M. Cohen, Cranford, NJ (US); Amanda J. Rogers, Asbury, NJ (US); Changxia Yuan, Warren, NJ (US); Jason J. Zhu, East Brunswick, NJ (US); Chao Hang, Monmouth Junction, NJ (US); Daniel S. Treitler, Cranford, NJ (US); Adam Joseph Freitag, Hopewell, NJ (US); Geoffrey Eugene Purdum, Freehold, NJ (US); Miao Yu, Malvern, PA (US); Melda Sezen Edmonds, Princeton, NJ (US); Siwei Guo, Vacaville, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 728 days.

(21) Appl. No.: 17/299,087

(22) PCT Filed: Dec. 3, 2019

(86) PCT No.: PCT/US2019/064137
§ 371 (c)(1),
(2) Date: Jun. 2, 2021

(87) PCT Pub. No.: WO2020/117739
PCT Pub. Date: Jun. 11, 2020

(65) Prior Publication Data
US 2022/0064205 A1    Mar. 3, 2022

Related U.S. Application Data

(60) Provisional application No. 62/775,094, filed on Dec. 4, 2018.

(51) Int. Cl.
| | | |
|---|---|---|
| *C07H 21/00* | (2006.01) | |
| *C07H 1/00* | (2006.01) | |
| *C07H 19/16* | (2006.01) | |
| *C07H 19/20* | (2006.01) | |

(52) U.S. Cl.
CPC .............. *C07H 21/00* (2013.01); *C07H 1/00* (2013.01); *C07H 19/16* (2013.01); *C07H 19/20* (2013.01)

(58) Field of Classification Search
CPC .......... C07H 21/00; C07H 1/00; C07H 19/16; C07H 19/20; C07H 21/02; C07H 19/167
See application file for complete search history.

(56) References Cited

U.S. PATENT DOCUMENTS 10,604,542 B2    3/2020    Glick et al.

FOREIGN PATENT DOCUMENTS

| WO | 17123669 A1 | 7/2017 | |
| WO | WO-2017123669 A1 * | 7/2017 | ......... A61K 31/7084 |
| WO | 19200273 A1 | 10/2019 | |

OTHER PUBLICATIONS

Knouse et al. Unlocking P(V): Reagents for chiral phosphorothioate synthesis. Science, 361(6408), 1234-1238. https://doi.org/10.1126/science.aau3369 (Year: 2018).*
Monticelli et al. Recent advancements on the use of 2-methyltetrahydrofuran in organometallic chemistry. Monatshefte Für Chemie—Chemical Monthly, 148(1), 37-48. https://doi.org/10.1007/s00706-016-1879-3 (Year: 2016).*
Richaud, A., Barba-Behrens, N., & Méndez, F. Chemical reactivity of the imidazole: a semblance of pyridine and pyrrole? Organic Letters, 13(5), 972-975. https://doi.org/10.1021/ol103011h (Year: 2011).*
Kojima, Naoshi, et al., "Synthesis of ribonucleic guanidine: replacement of the negative phosphodiester linkages of RNA with positive guanidinium linkages", Tetrahedron, 2002, vol. 58, pp. 867-879.
Mellal, D., et al. "Synthesis and biological evaluation of non-isomerizable analogues of Ala-tRNAAla" Org. Biomol. Chem. vol. 11(36) pp. 6161-6169 (2013).

* cited by examiner

*Primary Examiner* — Yih-Horng Shiao
*Assistant Examiner* — Hoi Yan Lee
(74) *Attorney, Agent, or Firm* — Roy Issac

(57) ABSTRACT

The invention generally relates to an improved processes for the preparation of a cyclic dinucleotide which is useful as a STING agonist of the following formula (I), involving the use of compounds A and B.

17 Claims, No Drawings

PROCESS FOR THE PREPARATION OF A CYCLIC DINUCLEOTIDE

CROSS-REFERENCE TO RELATED APPLICATIONS

This application is a national phase application under 35 U.S.C. § 371 of International Patent Application No. PCT/US2019/064137, filed Dec. 3, 2019, which claims priority to U.S. Provisional Application Ser. 62/775,094, filed Dec. 4, 2018, the contents of which are specifically incorporated fully herein by reference.

FIELD OF THE INVENTION

The invention generally relates to an improved processes for the preparation of a cyclic dinucleotide which is useful as a STING agonist.

BACKGROUND OF THE INVENTION

There is disclosed an improved processes for the preparation of Compound I of the formula

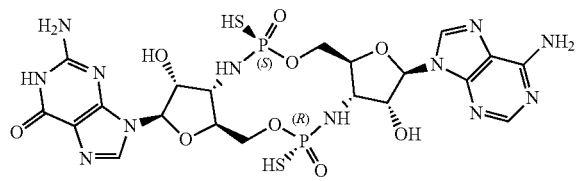

(I)

Compound I, compositions comprising Compound I, and an alternate process of preparing Compound I are disclosed in U.S. Ser. No. 15/748,685 filed Jan. 30, 2018, which is assigned to the present assignee and is incorporated herein by reference in its entirety. Compound I may be useful in the treatment of conditions associated with STING activity alone and in combination with other anticancer agents for the treatment of various types of cancer.

SUMMARY OF THE INVENTION

In a first aspect, the invention provides a process for preparing Compound I of the formula:

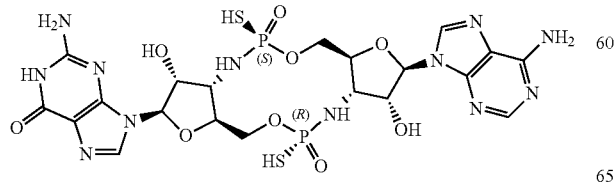

(I)

comprising the steps of a) reacting Compound 1 in DMF with TBSCl and Et$_3$N

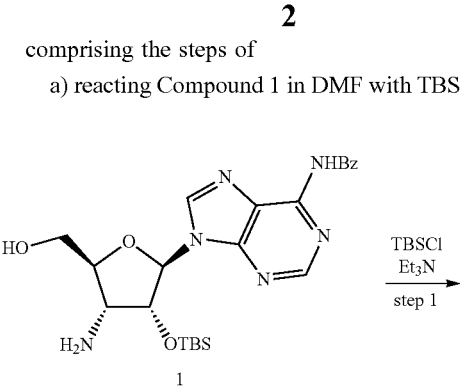

to afford Compound 2;

b) reacting Compound 2 with a base such as imidazole, DBU, diisopropylethylamine, triazole, tetrazole or metal alkoxide bases in a solvent such as THF, 2-MeTHF, MeCN or DMF, and then with Compound A to afford Compound 3

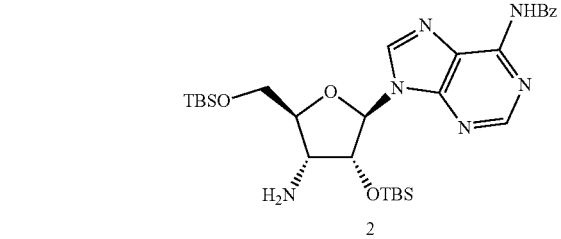

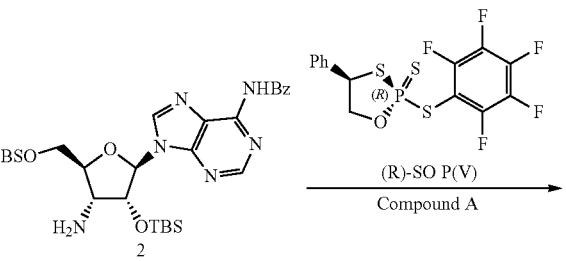

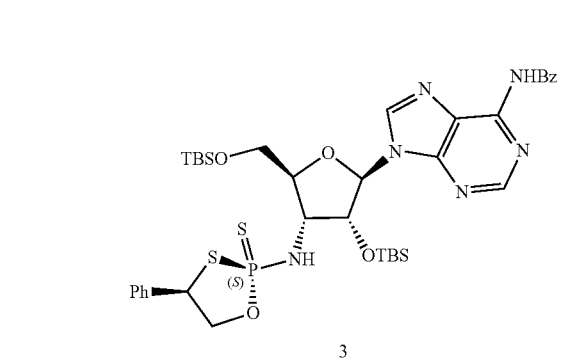

c) then, dissolving Compound 3 and Compound 9 in a solvent such as THF, MeCN or DMF and subsequently adding a base such as potassium t-butoxide, DBU or other metal allkoxide bases, followed by quenching with an appropriate acid such as acetic acid.

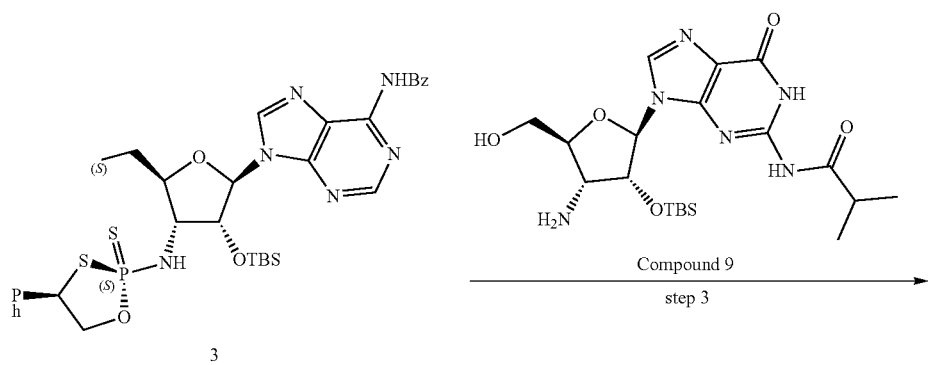
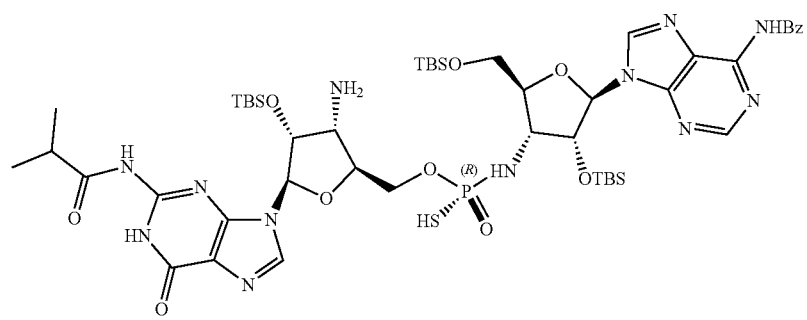
to afford Compound 4;
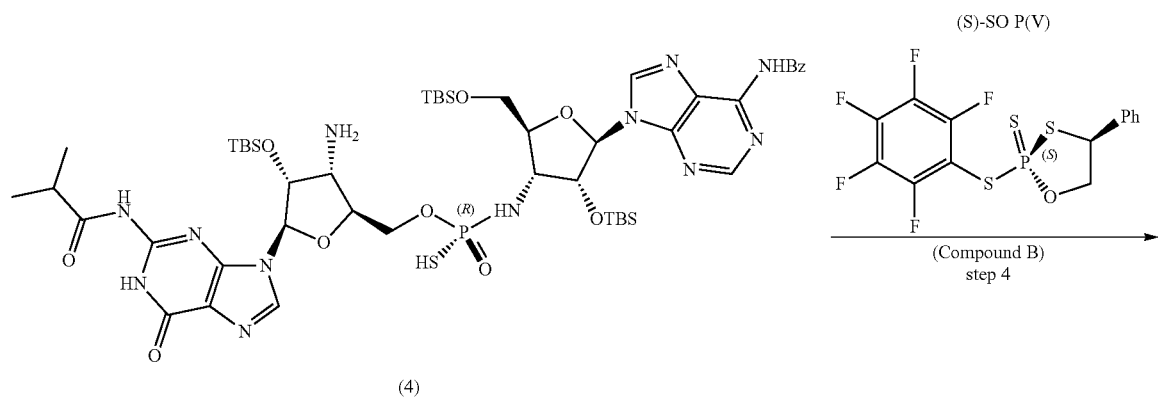
d) subsequently reacting Compound 4 in a solvent such as THF, 2-MeTHF, MeCN or DMF, and then adding a base such as imidazole, DBU, triazole, tetrazole, diisopropylethylamine or a metal alkoxide base, followed by the addition of Compound B to afford Compound 5 of the formula

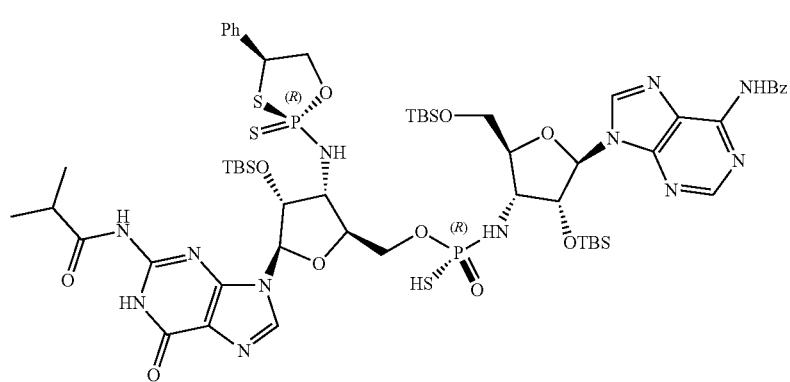

5 e) subsequently treating a solution of compound 5 in a solvent such as THF, MeTHF, or MeCN, with an acid such as TFA, MSA, p-TSA or utilizing a fluoride deprotection, to afford Compound 6 of the formula

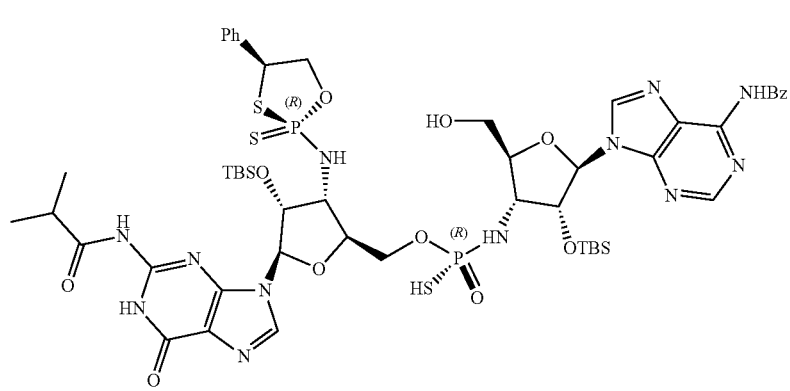

6 f) which is solubilized with a suitable solvent such as THF, MeCN, NMP or DMF and then mixed with a suitable base such as lithium t-butoxide, potassium t-butoxide, DBU, LiHMDS or other HMDS bases or other metal alkoxide bases, followed by stirring and quenching with a suitable quenching solution such as a glacial acetic acid in MeCN to afford Compound 7 of the formula

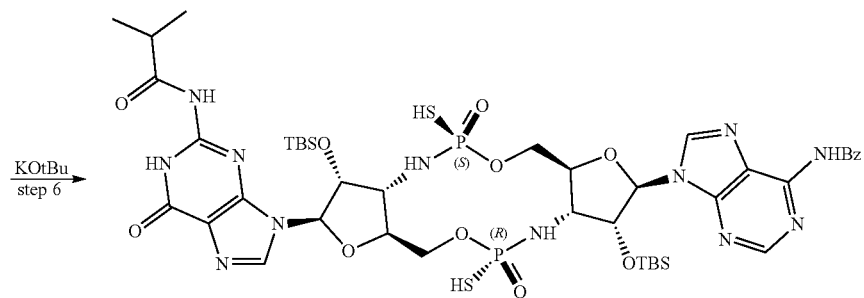

7 g) which is subsequently mixed with a suitable base such as methylamine, ammonia or other alkylamine bases, stirred and concentrated to afford Compound 8 of the formula

8

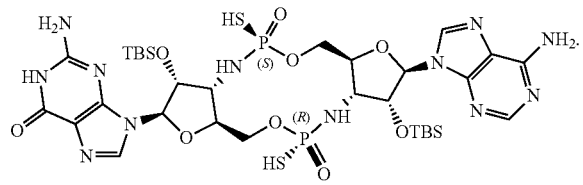

In a second aspect of the invention, there are provided novel intermediate compounds and diastereomers thereof as shown in the table below. While the compounds are shown with specific protecting groups, i.e., Bz for the amine substituent and TBS for the alcohol substituents; a broader range of protecting groups or none at all can be employed. For the amine protecting group (X), protecting groups can be selected from amides, thioamides, sulfonamides carbamates, imines, formamidines, alkyl (benzyl, allyl for example), phosphates and silyl compounds. For the alcohol protecting groups (Y), protecting groups can be selected from silyl, alkyl (allyl or benzyl, for example), alkoxymethyl ethers (TOM, for example), alkoxyethyl ethers (cyanoethyl, for example) and esters. These lists of protecting groups are not considered to be limiting but would also include additional ones known to those skilled in the art. The leaving groups which are part of Compounds A and B can be selected from any of the reagents shown in U.S. Ser. No. 16/382,692 filed Apr. 12, 2019, incorporated herein in its entirety.

| Compound No. | Structure |
|---|---|
| 2 | 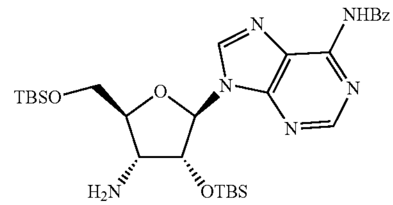 |
| 3 | 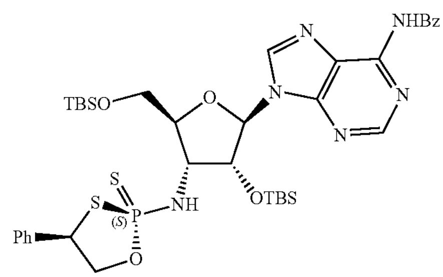 |
| 4 | 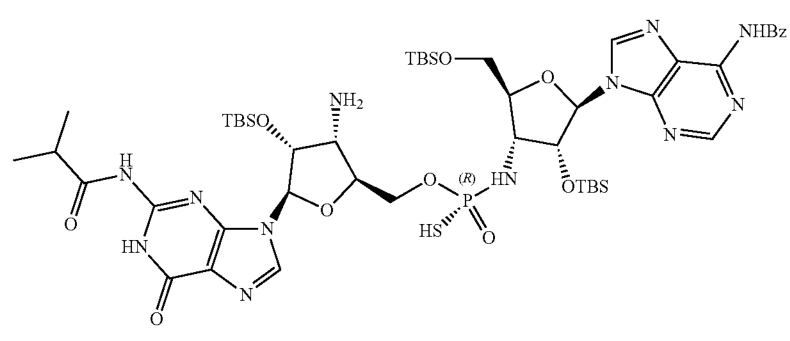 |

| Compound No. | Structure |
|---|---|
| 5 | *(structure of compound 5)* |
| 6 | *(structure of compound 6)* |
| 7 | *(structure of compound 7)* |
| 8 | *(structure of compound 8)* | which are used in the process of the invention.

Alternatively, Compound 8 can be prepared by the following series of steps
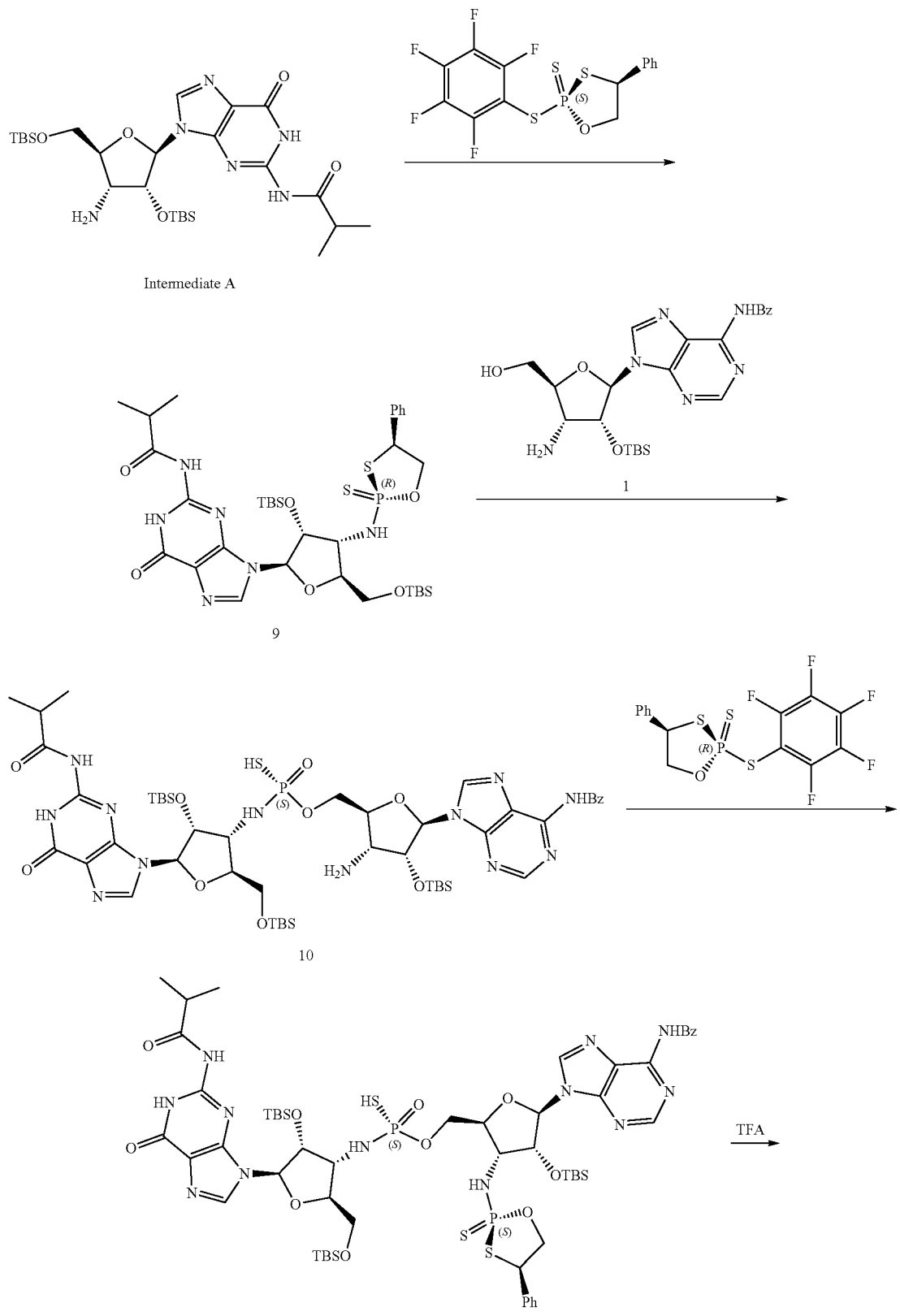

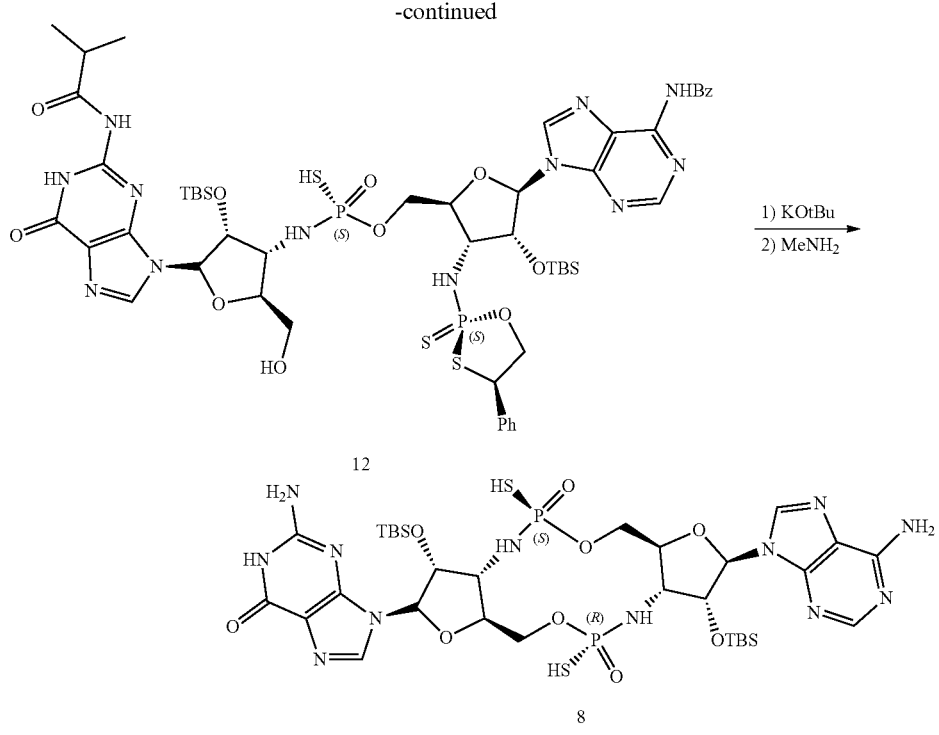

In one embodiment of the invention, there is disclosed the process wherein the base in step b) is imidazole, DBU, diisopropylethylamine, triazole, tetrazole or metal alkoxide bases.

In a preferred embodiment, the base in step b) is imidazole.

In one embodiment of the invention, there is disclosed the process wherein the solvent in step c) is THF, MeCN or DMF.

In a preferred embodiment, the solvent in step c) is THF.

In another embodiment of the invention, there is disclosed the process wherein the base in step c) is potassium t-butoxide, DBU or other alkoxide bases.

In a preferred embodiment, the base in step c) is sodium tert-pentoxide.

In another embodiment of the invention, there is disclosed the process wherein the solvent in step d) is THF, 2-MeTHF, MeCN or DMF.

In a preferred embodiment, the solvent in step d) is 2 Me-THF.

In another embodiment of the invention, there is disclosed the process wherein the base in step d) is imidazole, DBU, triazole, tetrazole, diisopropylethylamine or other alkoxides.

In a preferred embodiment, the base in step d) is imidazole.

In another embodiment of the invention, there is disclosed the process wherein the solvent in step f) is THF, MeCN, NMP, or mixtures thereof or DMF.

In a preferred embodiment, the solvent in step f) is a mixture of THF and NMP.

In another embodiment of the invention, there is disclosed the process wherein the base in step f) is potassium t-butoxide, lithium-t-butoxide, DBU or other metal alkoxide bases.

In a preferred embodiment, the base in step f) is lithium-t-butoxide

In another embodiment of the invention, there is disclosed the process wherein the base in step g) is methylamine, ammoniaor butylamine.

In a preferred embodiment, the base in step g) is methylamine

Advantages of the disclosed process include a greatly reduced length of synthesis as well as a reduction in the use of hazardous reagents such as $H_2S$ and $CCl_4$.

Additionally, the disclosed process is highly diastereoselective resulting in the ability to prepare a single (preferred) diastereoisomer with improved yield and quality relative to synthetic approaches that lack diastereoselectivity.

DETAILED DESCRIPTION OF THE INVENTION

Examples

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

The compounds included in this application are shown with specific stereochemistry, however, the methodology disclosed in the application can be implemented to provide any diastereomer.

For ease of reference, the following abbreviations may be used herein.

| Abbreviations | Name |
|---|---|
| 2-MeTHF | 2-methyltetrahydrofuran |
| ACN MeCN | acetonitrile |
| aq. | aqueous |
| Boc | t-butyl carbamate |
| Cbz | benzyl carbamate |
| conc. | concentrated |
| DBU | 1,8-Diazabicyclo[5.4.0]undec-7-ene |
| DCM | dichloromethane |
| DMF | dimethyl formamide |
| eq. | equivalents |
| Et$_3$N | triethylamine |
| EtOAc | ethyl acetate |
| EtOH | ethanol |
| h | hour(s) |
| HOAc | Acetic Acid |
| HPLC | high pressure liquid chromatography |
| H$_2$SO$_4$ | sulfuric acid |
| H$_3$PO$_4$ | Phosphoric acid |
| K$_2$HPO$_4$ | Dipotassium hydrogen phosphate |
| LCMS | Liquid chromatography-mass spectrometry |
| LiHMDS | Lithium hexamethyl disilazide |
| MeCN | Acetonitrile |
| MeOH | Methanol |
| MeNH$_2$ | Methylamine |
| MgSO$_4$ | Magnesium sulfate |
| MSA | methanesulfonic acid |
| MTBE | methyl t-butyl ether |
| Na$_2$SO$_4$ | Sodium sulfate |
| NaCl | Sodium chloride |
| NaOtAm | Sodium tert-pentoxide, sodium t-amylate |
| NLT | No less than |
| NMP | N-Methyl-2-pyrrolidone |
| NMR | nuclear magnetic resonance |
| pTSA | para-toluenesulfonic acid |
| rt/RT | room temperature |
| sat. | Saturated |
| TBAF | Tetra-n-butylammonium fluoride |
| TBSCL | tert-Butyldimethylsilyl chloride |
| TFA | trifluoroacetic acid |
| THF | Tetrahydrofuran |
| TLC | Thin-layer chromatography |
| UPLC | Ultra performance liquid chromatography |

Example 1

Preparation of Compound 2

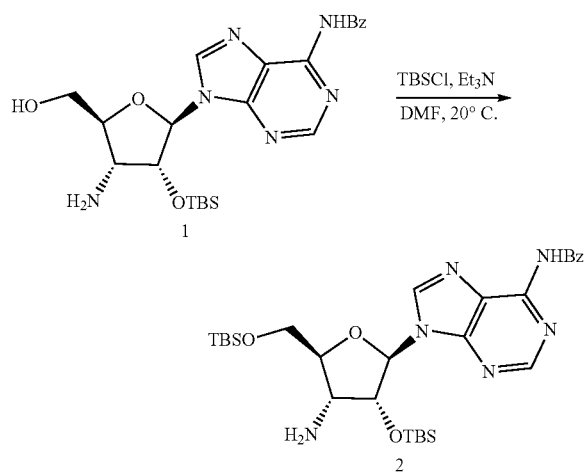

Compound 1 (25.0 g) was dissolved with DMF (180 mL). After addition of TBSCl (26.9 g, 3.35 equiv.) and Et$_3$N (29 mL, 4.0 eq) to the solution, the thick suspension was stirred overnight at rt. UPLC showed full conversion. The crude was thereafter diluted with MTBE, and washed with 5% H$_3$PO$_4$ solution (100 mL), 5% K$_2$HPO$_4$ (100 mL) and brine. The organic layer was separated, dried over Na$_2$SO$_4$, filtered and concentrated to a crude oil. The crude was purified on silica chromatography. The isolation product was a yellow amorphous solid (25.1 g, 81.2%). LCMS of 2: m/z (M+H)$^+$: 599.

Example 2

Preparation of Compound 3 (Lab Scale)

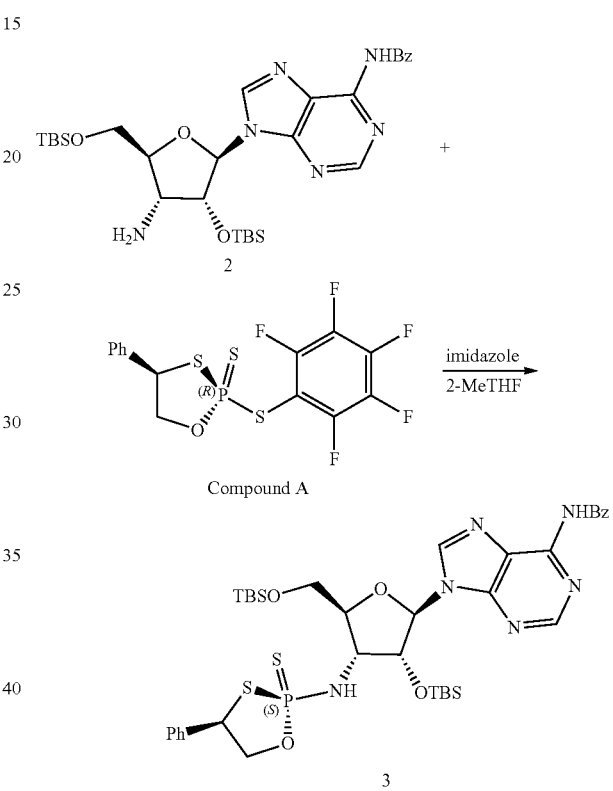

To a mixture of imidazole (2.37 g, 8 equiv., 34.9 mmol) and Compound 2 (2.90 g, 4.36 mmol, 90 mass %) was added MeCN (42 mL) at ambient temperature, followed by (R)—SO P(V) (Compound A) (3.25 g, 1.8 equiv., 7.84 mmol). The reactor was made inert by flushing with N$_2$ for 1 min.

After 2 h, the reaction mixture was concentrated and the resulting residue was purified by column chromatograph with 0-20% EtOAc in DCM, affording 2.82 g of white solids as Compound 3 (d.r. 98:2) in 77% yield. LCMS of 3: m/z (M+H)$^+$: 813.

Preparation of Compound 3 (Large Scale)

Compound 2 (1 kg, 1.0 equiv), imidazole (0.81 kg, 7.2 equiv) and 2-MeTHF are charged to a reactor. The reaction mixture is stirred until complete dissolution. The reaction mixture is cooled to 0° C. and Compound A (1.25 kg, 1.8 equiv) is charged to the reactor. The reaction is aged at 0° C. for no less than (NLT) 6 hours. The reaction is quenched with acetic acid (0.72 kg, 7.2 equiv) and then diluted with 2-MeTHF (4 L/kg) and n-hexane (3 L/kg). The resulting mixture is washed with water (6 L/kg) and DMF (4 L/kg)

and the aqueous layer is separated and discarded. The organic layer is then diluted with 2-MeTHF (1 L/kg) and then washed with aq. $K_2HPO_4$ (2 kg/kg in 6 L/kg water) and DMF (4 L/kg). Again the layers are separated and the aqueous layer is discarded. The organic layer is washed with aq. $K_2HPO_4$ (1.2 kg/kg in 6 L/kg water) and DMF (4 L/kg). Again the layers are separated and the aqueous layer is discarded. The organic layer is washed with aq. NaCl (1 w/w, 5.5 L/kg); and the aqueous layer is separated and discarded. The resulting mixture is diluted with methanol (6 L/kg) and the batch is concentrated to a total volume of 6 L/kg. The resulting mixture is diluted with methanol (6 L/kg). Water (0.75 L/kg) is charged to the reactor and crystalline seeds of Compound 3 are added. The batch is aged for 1 hr at 20° C. and water (2.75 L/kg) is added. The batch is aged and the resulting slurry is filtered. The cake is washed with 1:1 MeOH:Water (4 L/kg) and dried under reduced pressure at 40° C. The dry-cake is dissolved in toluene (5 L/kg) and heated to 40° C. The batch is cooled to 20° C. over 90 minutes. Crystalline seeds of Compound 3 are charged and aged for 4 hrs at 20° C. n-heptane (15 L/kg) is charged to the reactor over 2 hrs and aged at 20° C. for 1 hr. The resultant slurry is filtered and washed with 3:1 n-Heptane:toluene (4 L/kg). The solid is dried under reduced pressure at 50° C., affording 1.05 kg white solid as compound 3 in 77% yield.

Example 3

Preparation of Compound 4 (Lab Scale)

Intermediate Compound 9 (0.408 g, 1.35 equiv., 0.830 mmol, 95 wt %) and Compound 3 (0.500 g, 0.615 mmol) were dissolved in THF (5.0 mL) at 45° C., and the solvent was removed by blowing nitrogen into the reactor. THF (7.5 mL) was added into the residue, and the resulting mixture was warmed at 45° C. to dissolve most of the solids before cooling to ambient temperature. Potassium tert-butoxide (1 mol/L) in THF (1.84 mL, 3.0 equiv., 1.84 mmol) was slowly added over a period of 5 min. After 1.5 h, additional potassium tert-butoxide (1 mol/L) in THF (0.31 mL, 0.5 equiv., 0.31 mmol) was added into the reaction mixture, and the mixture was mixed for 0.5 h. The reaction mixture was then quenched by addition of acetic acid (0.15 mL, 4 equiv.). The mixture was concentrated, and the resulting residue was purified by column chromatograph with 0-10% MeOH in DCM, affording 0.46 g of white solids as Compound 4 in 65% yield. LCMS of Compound 4: m/z (M+H)$^+$: 1143.

Preparation of Compound 4 (Large Scale)

A slurry of THF (12.7 L, KF<100 ppm) and compound 9 (0.786 kg, 95 wt %, 1.1 equiv) was heated at 40-55° C., and concentrated under vacuum to 3-4 L of a batch volume. Dry THF (KF<100 ppm) was added to the initial batch volume (12.7 L). The mixture was then cooled to 0° C., and intermediate 3 (1.27 kg, 93 wt %, 1.0 equiv) was added. A solution of sodium t-pentoxide in THF (2.3 L, 2.3 M, 4.0 equiv) was then charged over a period of 30 min at ≤5° C. The mixture was aged at 0-5° C. until the reaction completed. Acetic acid (469 g, 5.0 equiv) was added to quench the reaction at ≤10° C. The resulting mixture was treated with a solution of monobasic sodium phosphate (10 wt %, 12.7 L). The layers were partitioned and the organic layer was washed with a solution of monobasic sodium phosphate (10 wt %, 7.6 L). The layers were partitioned and the resulting organic layer was distilled to 10 L under vacuum maintaining the batch temperature at 10-20° C. Acetonitrile (3.8 L) was added. A constant volume distillation was performed with the batch volume~12.7 L under vacuum at 10-20° C. The distillation ended when the solvent ratio of THF/acetonitrile reached ≤10% v/v. The batch was warmed to 20° C., and water was charged over a period of 30 min until KF of the batch was in the range of 35-50%. The slurry was aged for 1 h prior to filtration. The cake was washed with a mixture of acetonitrile/water (75/25 v/v, 2.54 L×2), acetonitrile (2.54 L×2), and dried in vacuum at ≤25° C., providing the product 1.16 kg (92 wt %) in 65% yield.

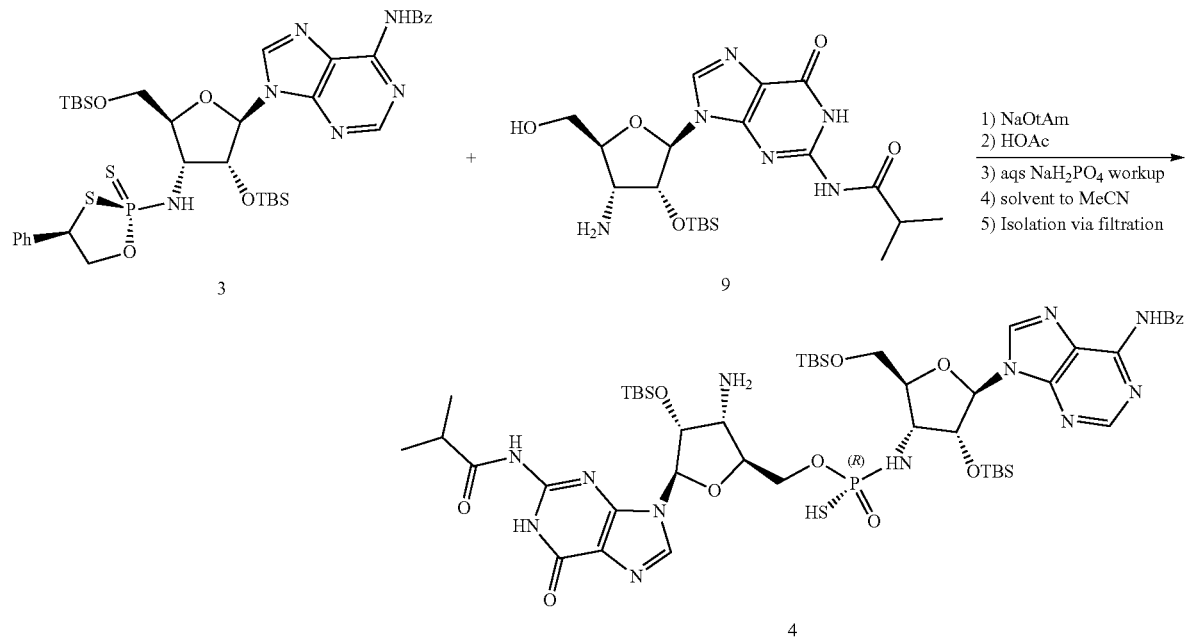

Example 4

Preparation of Compound 5 (Lab Scale)

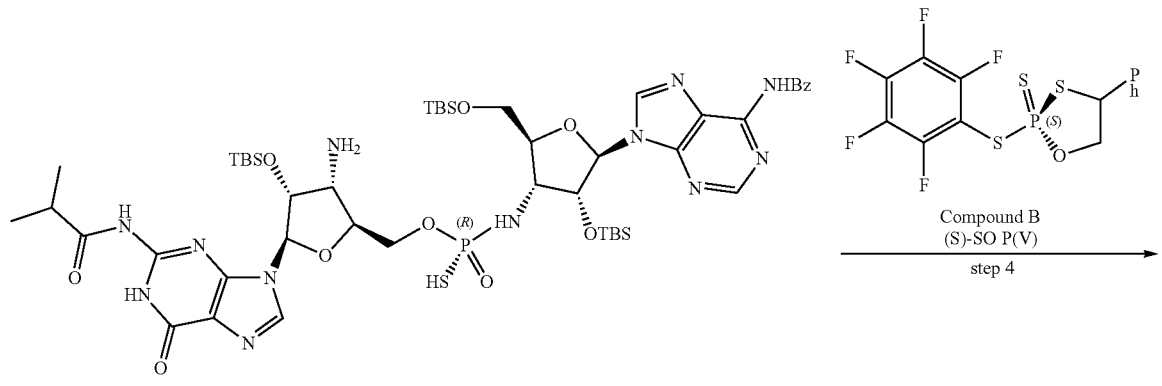

4

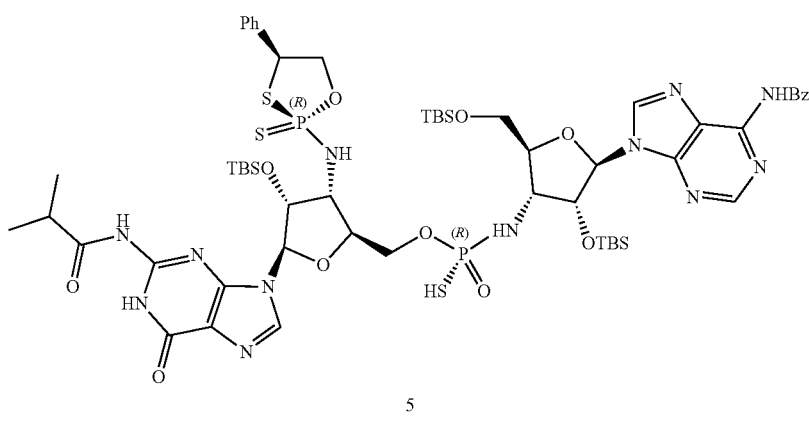

5

To a solution of Compound 4 (0.150 g, 0.131 mmol) in THF (3.3 mL, 22 v) was added imidazole (71 mg, 8 equiv., 1.05 mmol) at ambient temperature, followed immediately by (S)—SO P(V) (136 mg, 2.5 equiv., 0.328 mmol). The reactor was then made inert by flushing with $N_2$ for 1 min. After 1 h, imidazole (50 mg) and (S)—SO P(V) (50 mg) were added. After 4 h of last charge, (S)—SO P(V) (50 mg) was added and the mixture was agitated for 1 h, and was then concentrated. The residue was purified by column chromatograph with 0-20% MeOH in DCM, providing Compound 5 as a white solid (148 mg, 81% yield). LCMS of Compound 5: m/z $(M+H)^+$: 1357.

Example 4a

Preparation of Compound 6 (Lab Scale)

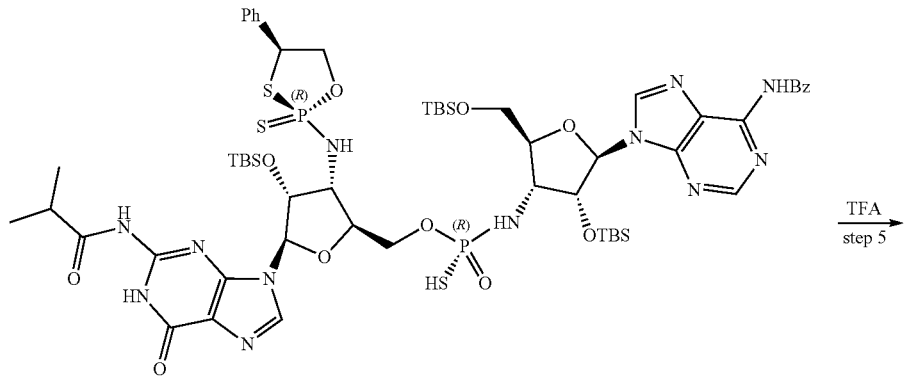

5

-continued

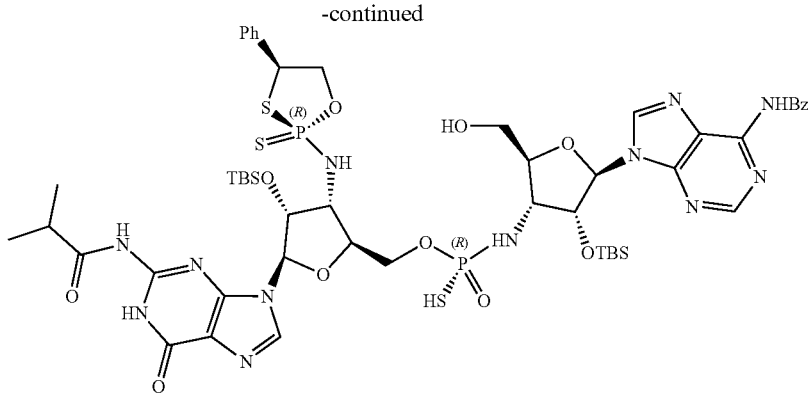

6

Water (0.15 mL) was added in a solution of 5 (0.15 g, 0.11 mmol) in DCM (3 mL, 20 v), followed by trifluoroacetic acid (0.30 mL, 4.0 mmol). The mixture was stirred at ambient temperature for 2 h, was then diluted with DCM (2 mL), and the resulting mixture was washed with aqueous solution of $K_2HPO_4$ (10%, 3 mL×2). The organic phase was dried over $MgSO_4$, and concentrated. The resulting residue was purified by column chromatograph with 0-20% MeOH in DCM, providing 6 as white solids (66 mg, 48% yield). LCMS of 6: m/z (M+H)$^+$: 1243.

Preparation of Compound 6 (Large Scale)

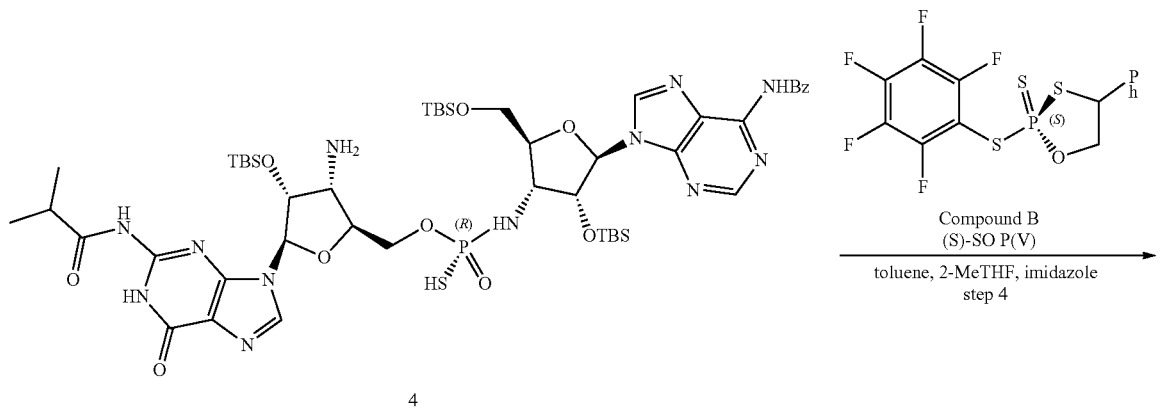

4

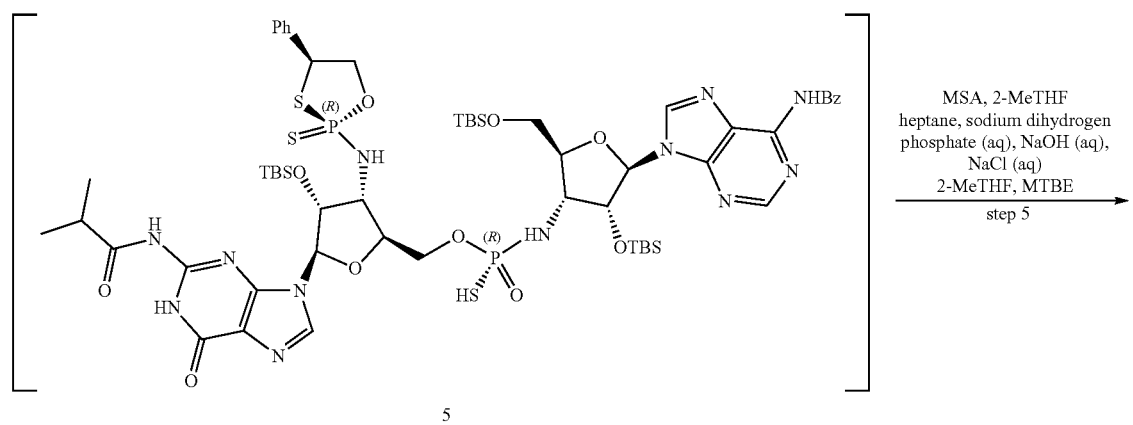

5

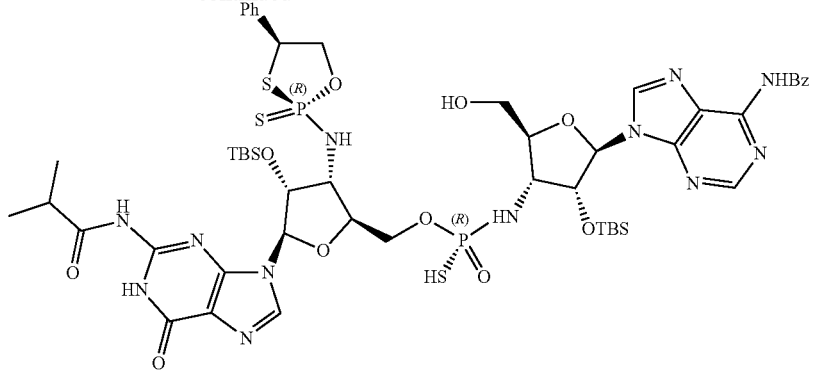

6

Preparation of Compound 6 (Large Scale)

An anhydrous solution of Compound 4 (1.0 equiv) in 2-MeTHF (5 L/kg) plus imidazole (8.0 equiv) is prepared. The solution is cooled to 0° C. and solid Compound B is stirred into the reaction in a single portion. The solution is aged for 16 h or until Compound 4 is consumed. The reaction stream is diluted with additional MeTHF (4 L/kg), then MSA (11.0 equiv) is stirred in as a solution in 2-MeTHF (5 L/kg), while maintaining the internal temperature below 0° C. The solution is aged 5 h at −5° C. or until Compound 5 is consumed. The reaction is quenched with pH 4.5 aqueous sodium phosphate buffer (4 L/kg), then the aqueous layer is separated. The organic layer is washed twice more with additional pH 4.5 aqueous sodium phosphate buffer (2×4 L/kg), then washed with saturated aqueous sodium chloride (4 L/kg). The washed organic layer is concentrated under reduced pressure to a final volume of 5 L/kg, then the water content of the stream is reduced to NMT 0.7 wt % using 2-MeTHF codistillation or molecular sieves. MTBE (15 L/kg) is stirred in dropwise over the course of 1 h and the resultant slurry is aged for NLT 1 h at 20° C. The slurry is filtered and the cake is washed with MTBE (2×4 L/kg), then the resultant solid is dried at −30° C. under reduced pressure with a slow flow of $N_2$.

The large scale production of Compound 6 does not include an isolation of Compound 5 which differs from the lab scale shown above.

Example 5

Preparation of Compound 7 (Lab Scale)

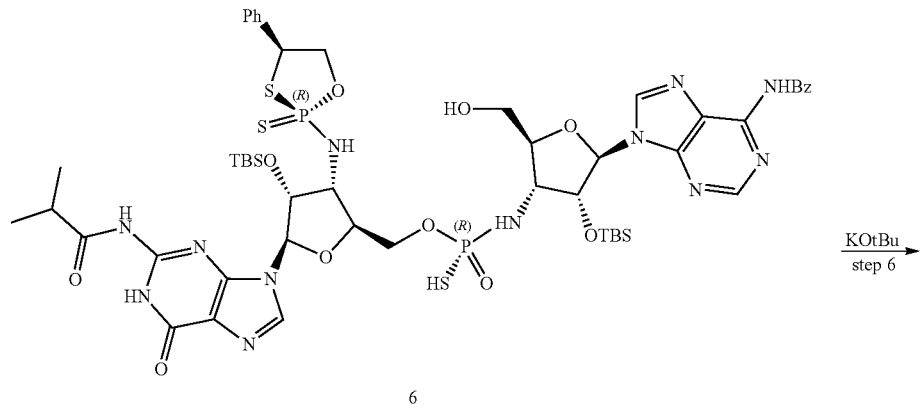

6

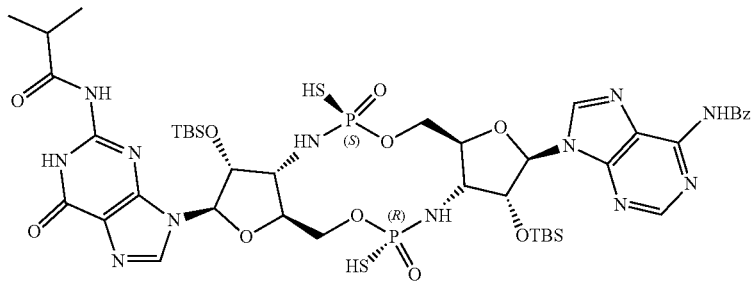

7

To a solution of Compound 6 (5.0 mg 0.0040 mmol) in THF (1.0 mL) (alternate solvents: MeCN, DMF) was slowly added potassium tert-butoxide (1 mol/L) in THF (0.012 mL, 3.0 equiv., 0.012 mmol) at ambient temperature. The mixture was stirred for 17 h at temperature. The reaction mixture was then quenched with a solution of HOAc in MeCN (5% v/v, 0.3 mL). HPLC analysis indicated that a major peak was formed as the desired product 7. LCMS of 7: m/z (M+H)$^+$: 1107. The resulting stream was used for subsequent step 7 without further purification.

Preparation of Compound 7 (Large Scale)

To a reactor under nitrogen protection is charged THF (15 L, 15 L/kg) and the temperature is adjusted to 20° C. Sequentially BMT-433600 (1.0 kg, 1.0 equiv, LR) is charged into the reactor. The solution is distilled at 20-25° C. under vacuum (150-200 torr) to 5 L/kg, until KF of the mixture is no more than 600 ppm. If the KF cannot be reached, additional THF (10 L, 10 L/kg) is added and the distillation repeated. To the solution is added NMP (7.5 L, 7.5 L/kg) followed by LiOtBu (3.0 L, 3.0 eq., 1 M in THF) in portions to reactor, maintaining internal temperature 20-30° C. After 1 h, acetic acid (241 g, 5.0 equiv) is added to quench the reaction. After 15 min, the mixture is treated with water (5 L, 5 L/kg), cyclohexane (10 L, 10 L/kg) and aged at 20-30° C. for 0.5 h. The layers are partitioned and to the aqueous layer is added 2-MeTHF (10 L, 10 L/kg) and 20 wt % NaCl aqueous solution (3.0 L, 3.0 L/kg). The resulting mixture is aged at 20-30° C. for 0.5 h. The layers are partitioned and the aqueous layer is back extracted with 2-MeTHF (10 L, 10 L/kg). The combined the organic layers are then concentrated to 2-3 L/kg at 20-30° C. and 100 torr. The resulting stream is used in the next step without further purification.

Example 6

Preparation of Compound 8

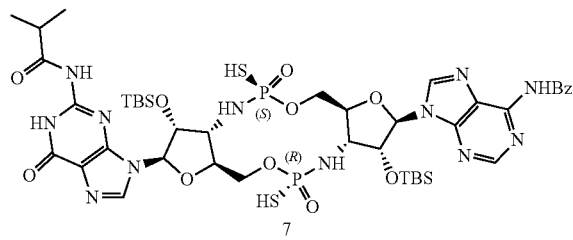

7

| MeNH$_2$
| step 7
↓

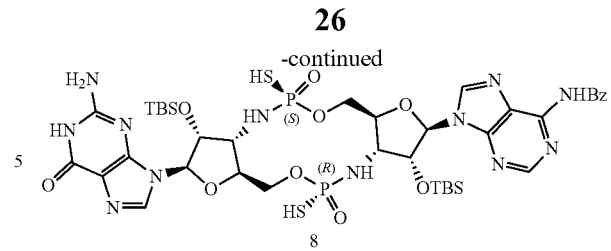

8

To the above solution from step 6 was added a solution of methylamine in EtOH (33 wt %, 0.5 mL). The mixture was stirred at ambient temperature for 0.5 h, and then concentrated. The resulting residue was purified by preparative TLC with 15% MeOH in DCM, providing Compound 8 as a white solid (1.0 mg, 27% yield over two steps 6 and 7). LCMS of Compound 8: m/z (M+H)$^+$: 933.

Preparation of Compound 8 (Large Scale)

To a solution of compound 7 in NMP (2-3 L/kg) is charged 33 wt % MeNH$_2$ in Ethanol (1 L/kg, 10 equiv. MeNH$_2$). The reaction mixture is aged for 5 hrs at 20° C. or until Compound 7 is fully consumed. The reaction is quenched with 6 N aq. HCl (6 equiv.) and citric acid (1 equiv.) in water (1.5 L/kg) is charged to the reaction mixture. The resultant slurry is aged for 2 hrs at 20° C. The slurry is filtered and the cake is washed with tetrahydrofuran (3 L/kg) followed by water (3 L/kg). The cake is dried at 55° C. under reduced pressure with a slow flow of nitrogen. The dry-cake is dissolved in THF (4 L/kg), water (4 L/kg) and NH$_4$OH (3 equiv.) and then aged at 20° C. for 1 hr. Citric acid (3 equiv.) in water (2 L/kg) is charged to the reactor and the resultant slurry is aged at 20° C. for 2 hrs. The slurry is filtered and the cake is washed with THF (2×3 L/kg). The cake is dried at 55° C. under reduced pressure with a slow flow of nitrogen.

Example 7

Preparation of Compound I (Lab Scale)

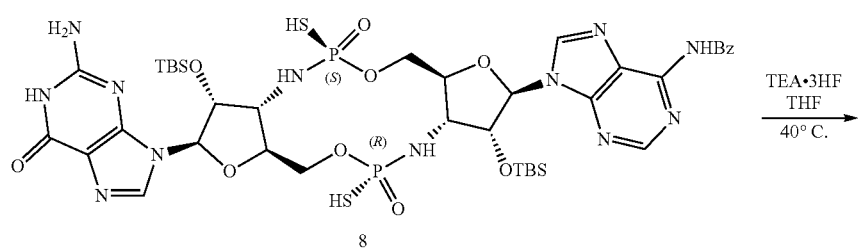

8

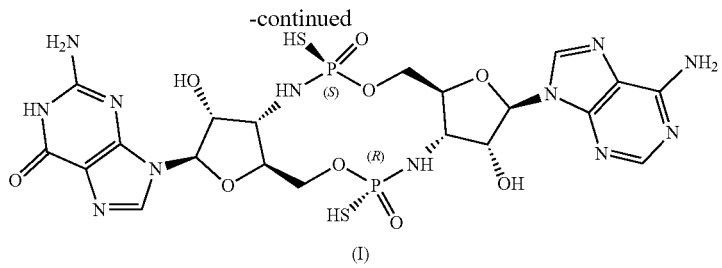

(I)

Intermediate 8 (0.25 g, 0.25 mmol) was suspended in THF (1.25 mL, 5 v) at ambient temperature. Triethylamine trihydrofluoride (0.41 mL, 10 equiv, 2.51 mmol) was added to the suspension resulting in a homogeneous solution. Triethylamine (0.18 mL, 5 equiv, 1.26 mmoL) was then added, and the solution was heated to 40° C. The reaction mixture was aged at 40° C. for 6 hours to afford >90% in-process yield of Compound I.

Preparation of Compound I (Large Scale)

Into a reactor, intermediate 8 and 3 eq TBAF trihydrate are charged, followed by acetonitrile; the batch is heated to 50° C. and held at temperature for no less than 18 hours. At the end of reaction, batch is cooled to room temperature and the crude product is purified to give Compound (I) in 75-80% yield.

Spectra Data:

Compound 2: $^1$H NMR (400 MHz, CDCl3) δ 9.12 (s, 1H), 8.80 (s, 1H), 8.56 (s, 1H), 8.02 (d, J=7.5 Hz, 2H), 7.62-7.49 (m, 3H), 6.11 (s, 1H), 4.40 (d, J=4.3 Hz, 1H), 4.11 (dd, J=11.5, 2.1 Hz, 1H), 3.98-3.89 (m, 2H), 3.61 (dd, J=8.3, 4.6 Hz, 1H), 1.60 (brs, 2H), 0.95 (s, 18H), 0.79 (s, 1H), 0.22 (s, 3H), 0.15 (s, 3H), 0.14 (s, 3H), 0.13 (s, 3H). $^{13}$C NMR (100 MHz, CDCl3) δ 164.6, 152.6, 151.0, 149.3, 141.6, 133.9, 132.7, 128.8, 127.8, 123.2, 90.0, 85.1, 77.9, 61.9, 52.2, 26.1, 25.8, 18.6, 18.1, −4.4, −4.9, −5.3, −5.4.

m/z (M+H)$^+$ 600.

Compound 3: $^1$H NMR: 1H NMR (400 MHz, CDCl3) δ 9.12 (s, 1H), 8.63 (s, 1H), 8.38 (s, 1H), 7.89 (d, J=7.6 Hz, 2H), 7.46 (t, J=7.2 Hz, 1H), 7.38 (t, J=7.2 Hz, 2H), 7.22 (br s, 5H), 6.02 (d, J=2.0 Hz, 1H), 5.10-4.87 (br m, 1H), 4.55-4.36 (br m, 3H), 4.12 (q, J=9.7 Hz, 1H), 4.07-4.00 (br m, 2H), 3.98 (br d, J=11.9 Hz, 1H), 3.80 (dd, J=11.9, 2.8 Hz, 1H), 0.80 (s, 9H), 0.80 (s, 9H), 0.00 (s, 12H). $^{13}$C NMR (100 MHz, CDCl3) δ 164.7, 152.7, 151.2, 149.6, 141.5, 134.7, 134.6, 133.8, 132.8, 129.3, 129.2, 128.9, 127.9, 127.7, 123.3, 89.8, 84.9, 84.8, 76.6, 76.5, 74.2, 74.1, 61.9, 57.0, 56.9, 54.1, 26.2, 25.8, 18.6, 18.0, −4.7, −4.8, −5.1, −5.4. $^{31}$P NMR (160 MHz, CDCl3) δ 95.9.

m/z (M+H)$^+$ 813.

Compound 4: $^1$H NMR: (500 MHz, DMSO-d6) δ 12.24-11.76 (m, 2H), 11.13 (s, 1H), 8.74-8.35 (m, 4H), 8.25-8.19 (m, 1H), 7.99-7.89 (m, 2H), 7.65-7.52 (m, 1H), 7.51-7.41 (m, 2H), 6.09-5.99 (m, 1H), 5.77-5.67 (m, 1H), 5.14-5.05 (m, 1H), 4.55-4.44 (m, 1H), 4.32-4.21 (m, 1H), 4.20-4.06 (m, 3H), 3.98-3.71 (m, 4H), 3.30-3.25 (m, 2H), 2.87-2.73 (m, 1H), 1.09-0.99 (m, 6H), 0.80 (s, 9H), 0.74 (s, 9H), 0.68 (s, 9H), 0.00 (s, 6H), −0.01 (s, 3H), −0.06-−0.12 (m, 6H), −0.29-−0.34 (m, 3H). $^{13}$C NMR: (126 MHz, DMSO-d6) δ 180.3, 165.6, 154.8, 151.8, 151.7, 150.4, 148.5, 148.0, 141.6, 138.8, 133.3, 132.4, 128.5, 128.4, 125.6, 120.8, 88.6, 88.1, 85.0, 84.9, 80.5, 80.5, 76.0, 76.0, 73.1, 64.4, 64.4, 63.1, 53.4, 52.9, 34.6, 25.9, 25.6, 18.9, 18.8, 18.1, 17.7, 17.5, −5.0, −5.1, −5.2, −5.3, −5.5. $^{31}$P NMR (202 MHz, DMSO-d6) δ 59.9.

m/z (M+H)$^+$ 1143

Compound 5: $^1$H NMR (500 MHz, DMSO-d$_6$) δ 12.32-12.06 (m, 1H), 11.41-11.10 (m, 1H), 8.71 (s, 1H), 8.53-8.42 (m, 1H), 8.23-8.19 (m, 1H), 8.06 (br d, J=7.6 Hz, 2H), 7.66-7.62 (m, 1H), 7.57-7.47 (m, 5H), 7.31 (s, 2H), 7.31 (d, J=4.8 Hz, 2H), 6.21 (br t, J=11.4 Hz, 1H), 6.11 (d, J=3.5 Hz, 1H), 5.89 (d, J=5.5 Hz, 1H), 5.23 (br t, J=7.8 Hz, 1H), 5.04-4.92 (m, 1H), 4.62-4.57 (m, 1H), 4.48-4.40 (m, 1H), 4.38-4.20 (m, 4H), 4.19-4.14 (m, 1H), 3.87-3.69 (m, 3H), 2.92-2.83 (m, 1H), 1.96-1.89 (m, 1H), 1.84-1.76 (m, 2H), 1.36-1.26 (m, 2H), 1.07-1.04 (m, 3H), 0.86 (s, 9H), 0.82-0.79 (m, 9H), 0.75 (s, 9H), 0.10-0.03 (m, 9H), −0.01 (d, J=4.9 Hz, 6H), −0.17 (s, 3H). $^{31}$P NMR (202 MHz, DMSO-d6) δ 95.2, 57.8.

m/z (M+H)$^+$ 1357.

Compound 6: $^1$H NMR (500 MHz, DMSO-d6): δ 12.14 (s, 1H), 11.58 (br s, 1H), 11.22 (br s, 1H), 8.73 (d, J=6.4 Hz, 2H), 8.22 (s, 1H), 8.04 (d, J=7.3 Hz, 2H), 7.63 (m, 1H), 7.59-7.52 (m, 4H), 7.43-7.32 (m, 3H), 6.48 (dd, J=13.0, 10.5 Hz, 1H), 6.10 (d, J=3.0 Hz, 1H), 5.87 (d, J=5.1 Hz, 1H), 5.30 (dd, J=8.4, 5.7 Hz, 1H), 4.71 (t, J=6.0 Hz, 1H), 4.65-4.52 (m, 3H), 4.37 (q, J=9.5 Hz, 1H), 4.33-4.15 (m, 6H), 4.10-3.91 (m, 3H), 3.71 (m, 1H), 3.59 (m, 1H), 2.79 (quin, J=6.8 Hz, 1H), 1.09 (app t, 6H), (m, 18H), 0.80 (s, 9H), 0.75 (s, 9H), 0.06 (s, 3H), 0.02 (s, 3H), 0.00 (s, 3H), −0.15 (s, 3H). $^{13}$C NMR (125 MHz, DMSO-d6): δ 180.1, 165.6, 151.6, 151.5, 150.4, 148.8, 148.2, 142.2, 137.7, 135.2 (2 C), 133.4, 132.4, 128.8 (2 C), 128.7, 128.5 (2 C), 128.4 (3 C), 128.2 (2 C), 125.6, 120.3, 88.9, 87.5, 84.5, 82.1, 75.5, 73.9, 73.6, 65.6, 60.3, 55.9, 55.1, 52.8, 34.6, 25.8, 25.6 (6 C), 18.8, 17.7, −4.7, −4.9, −5.1, −5.2.

m/z (M+H)$^+$ 1243.

Compound 7: $^1$H NMR (400 MHz, DMSO-d$_6$) δ 12.13 (br s, 1H), 11.76-11.49 (m, 1H), 11.17 (br s, 1H), 9.10 (s, 1H), 8.73 (s, 1H), 8.10 (br s, 1H), 8.04 (d, J=10.0 Hz, 2H), 7.65-7.59 (m, 1H), 7.62 (t, J=10.0 Hz, 1H), 7.53 (t, J=10.0 Hz, 2H), 6.17 (s, 1H), 5.83 (s, 1H), 4.59 (br s, 1H), 4.22-4.07 (m, 4H), 4.07-3.94 (m, 4H), 3.87 (br dd, J=10.9, 3.1 Hz, 1H), 2.82 (dt, J=13.7, 6.8 Hz, 1H), 1.90 (s, 1H), 1.05 (d, J=10.0 Hz, 6H), 0.99 (s, 9H), 0.94 (s, 9H), 0.33 (s, 3H), 0.25 (s, 3H), 0.23 (s, 3H), 0.16 (s, 3H). $^{13}$C NMR: (101 MHz, DMSO-d6) δ 180.7, 172.5, 166.0, 155.4, 151.8, 150.6, 148.5, 148.4, 142.7, 134.0, 132.8, 129.0, 128.9, 125.9, 90.0, 81.4, 77.5, 76.0, 62.3, 53.6, 51.2, 34.8, 26.5, 26.4, 26.3, 23.0, 21.6, 19.2, 18.3, 18.2, −2.7, −3.7, −4.1, −4.2, −4.3.

$^{31}$P NMR (202 MHz, DMSO-d$_6$) δ 55.8, 52.4.

m/z (M+H)$^+$ 1107.

Compound 8: $^1$H NMR (500 MHz, DMSO-d$_6$) δ 8.88 (s, 1H), 8.34 (s, 1H), 7.87 (s, 1H), 6.01 (s, 1H), 5.75 (s, 1H), 4.50 (br s, 1H), 4.10-3.86 (m, 9H), 0.93 (s, 9H), 0.90 (s, 9H), 0.23 (s, 3H), 0.21 (s, 6H), 0.16 (s, 3H). $^{13}$C NMR: (126

MHz, DMSO-d6) δ 157.2, 154.0, 152.0, 150.7, 148.3, 147.2, 141.1, 134.9, 119.0, 116.3, 90.1, 89.2, 81.0, 79.9, 77.2, 75.7, 62.8, 61.0, 52.6, 51.0, 26.3, 26.3, 18.2, 18.1, −4.3, −3.8-4.4, −4.4. $^{31}$P NMR (202 MHz, DMSO-d6) δ 57.1, 53.9. m/z (M+H)$^+$ 933.
Compound I: $^1$H NMR (500 MHz, DMSO-d$_6$): δ 10.76 (br s, 1H), 8.73 (s, 1H), 8.31 (s, 1H), 7.80 (s, 1H), 6.54 (br s, 2H), 6.06 (s, 1H), 5.79 (s, 1H), 4.36 (br d, J=4.2 Hz, 1H), 4.25 (br d, J=10.5 Hz, 1H), 4.19 (br d, J=10.5 Hz, 1H), 4.10 (overlapped, 3H), 4.02 (br dd, J=10.2, 3.6 Hz, 1H), 3.95 (v br m, 1H), 3.90 (overlapped, 2H). $^{13}$C NMR (126 MHz, DMSO-d$_6$, 25° C.): δ 156.8, 153.9, 153.2, 150.5, 149.0, 148.1, 139.9, 134.3, 118.7, 116.3, 89.9, 88.6, 80.4, 79.2, 74.7, 73.3, 62.3, 61.2, 52.2, 50.8. $^{31}$P NMR (206 MHz, DMSO-d$_6$, 25° C.): δ 62.8. m/z (M+H)$^+$ 705.
Alternate Route to Compound 8 (Steps 1 and 2)
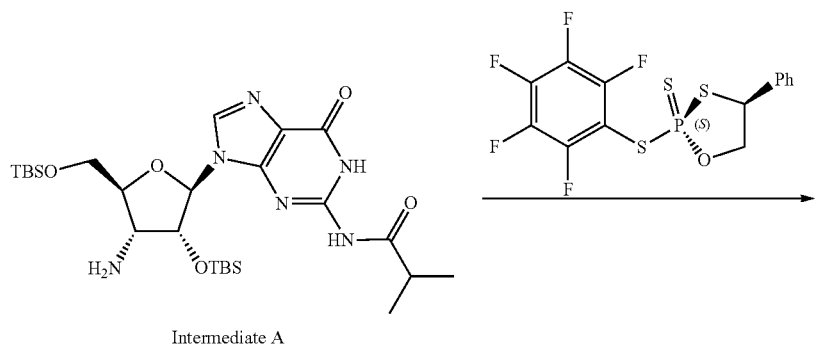
Intermediate A
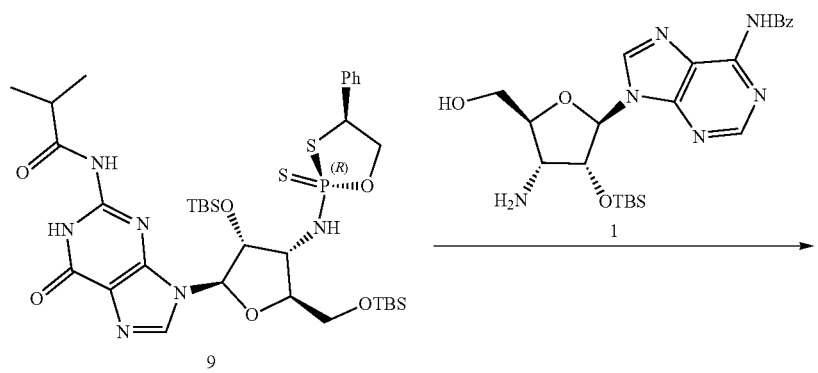
9
1
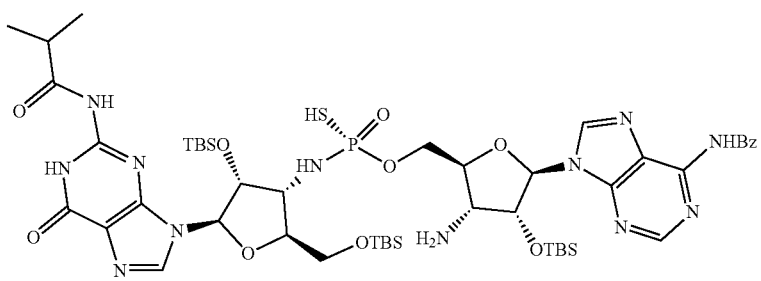
10

Step 1:

To a mixture of imidazole (1.93 g, 8 equiv., 28.3 mmol) and Intermediate A (2.04 g, 1.0 equiv., 3.51 mmol) was added MeCN (25 mL) at ambient temperature. The mixture was concentrated. MeCN (15 mL) was added into the resulting residue, followed by (S)—SO P(V) (Compound B) (2.85 g, 2.0 equiv., 7.02 mmol) under nitrogen atmosphere. After 2 h, the reaction mixture was concentrated and the resulting residue was purified by column chromatograph with 0-25% EtOAc in DCM, affording 1.80 g of white solids as Compound 9 (d.r. 97:3) in 65% yield; m/z (M+H)$^+$: 795.

Step 2:

Compound 9 (0.600 g, 1.0 equiv., 0.755 mmol) and compound 1 (0.345 g, 1.2 equiv., 0.906 mmol) were dissolved in THF (10.0 mL), and the solvent was removed by concentration under vacuum. THF (12 mL) was added into the resulting residue, and the mixture was cooled to 0° C. Potassium tert-butoxide (1 mol/L) in THF (2.3 mL, 3.0 equiv., 2.3 mmol) was slowly added over a period of 5 min. After the reaction mixture was stirred at 0° C. for 16 h, acetic acid (0.173 mL, 4.0 equiv.) was added. The reaction mixture was concentrated, and the resulting residue was purified by column chromatograph with 0-10% MeOH in DCM, affording 0.50 g of white solids as Compound 10 in 56% yield; LCMS of Compound 10 (M+H)$^+$: 1143.

comprising the steps of
a) reacting Compound 1 with TBSCl and Et$_3$N

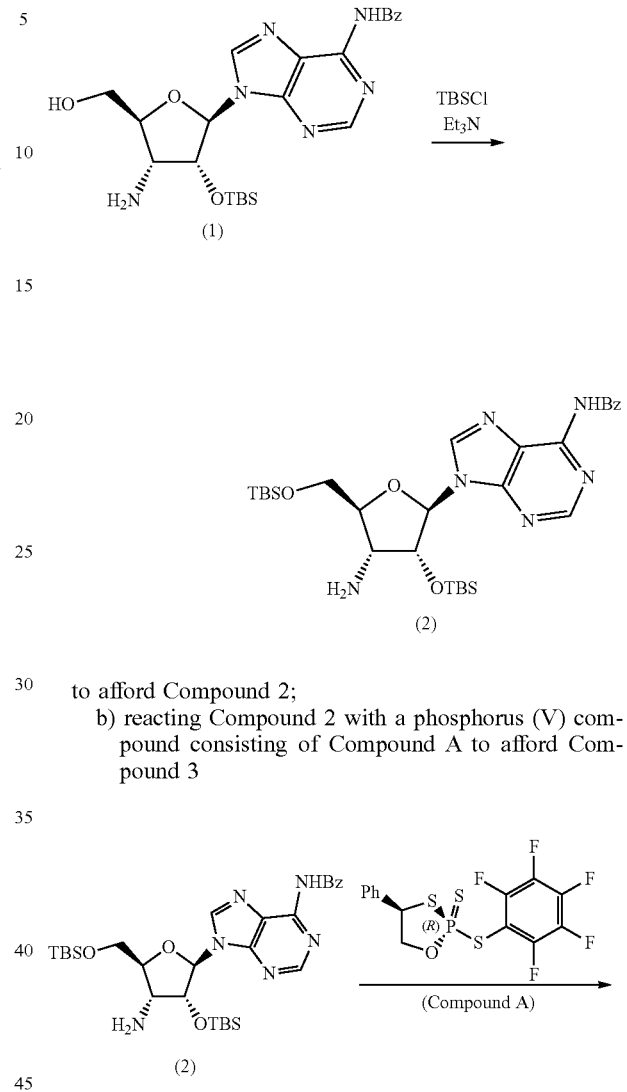

to afford Compound 2;
b) reacting Compound 2 with a phosphorus (V) compound consisting of Compound A to afford Compound 3

We claim:

1. A process for the preparation of Compound I having the formula

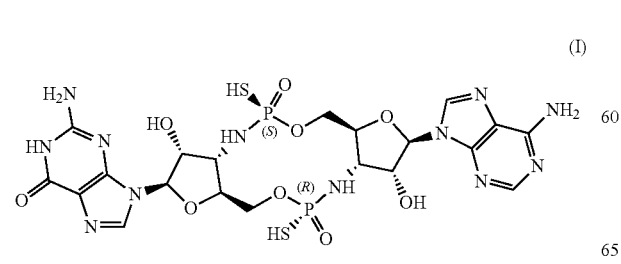

(I)

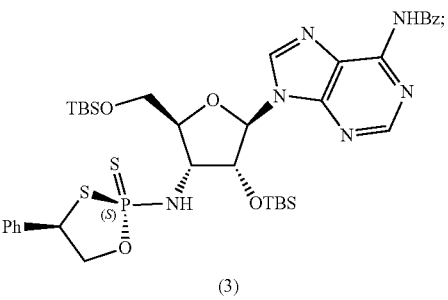

c) reacting Compound 3 and Compound 9
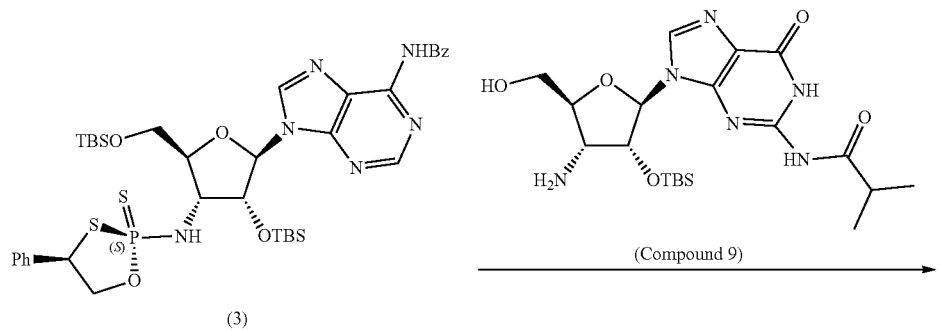
(3)    (Compound 9)
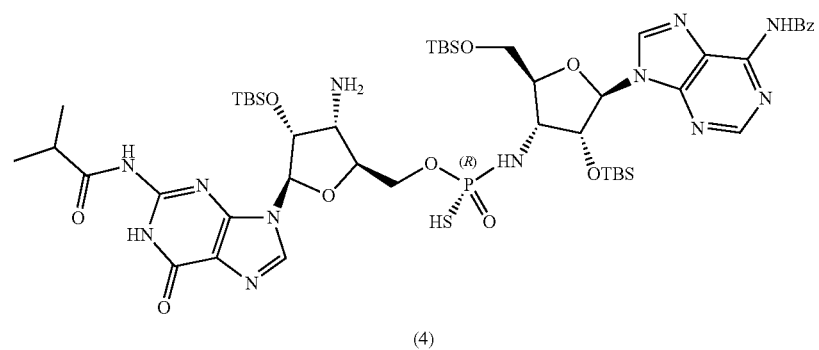
(4)
to afford Compound 4;
d) reacting Compound 4 in a solvent, and then adding a base, followed by the addition of a phosphorus (V) compound consisting of Compound B
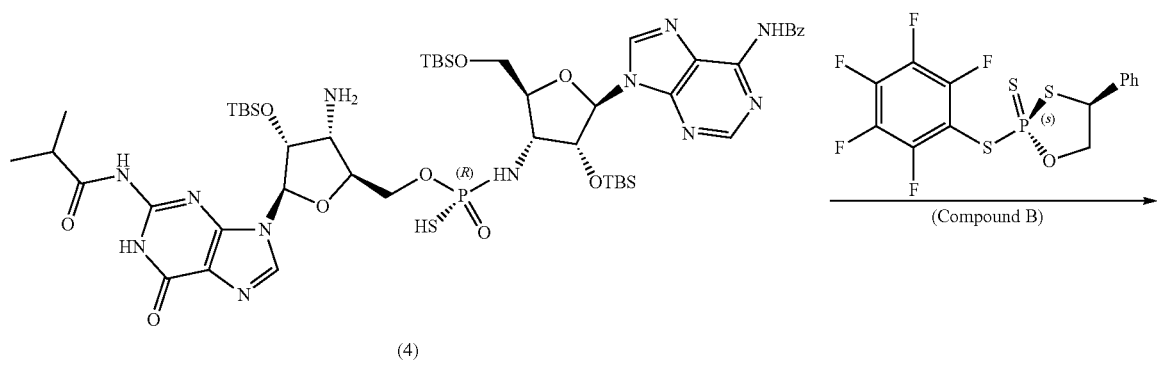
(4)    (Compound B)

to afford Compound 5 having the formula
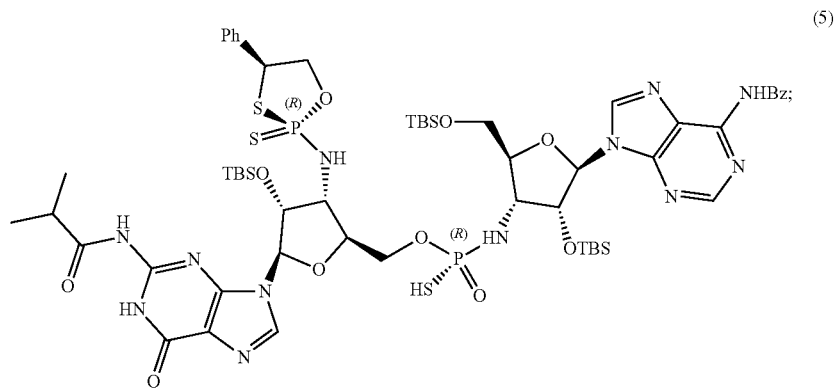
(5)
e) selectively deprotecting Compound 5 to afford Compound 6 having the formula
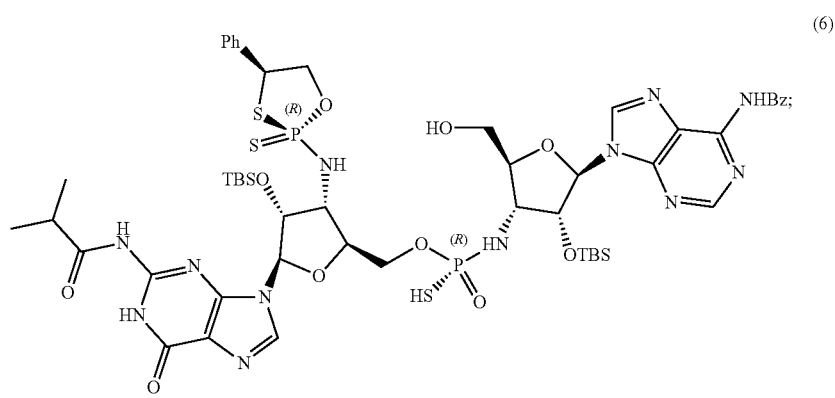
(6)
f) the Compound 6 is cyclized in a suitable solvent under basic conditions to afford Compound 7 having the formula
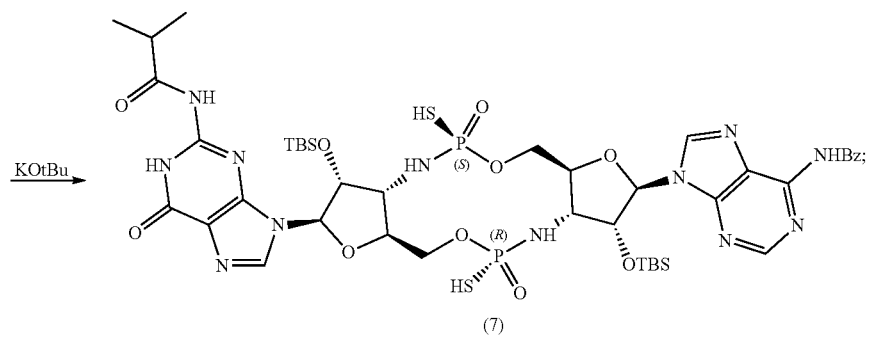
(7)

g) the Compound 7 is subsequently mixed in a suitable base, stirred and concentrated to afford Compound 8 having the formula

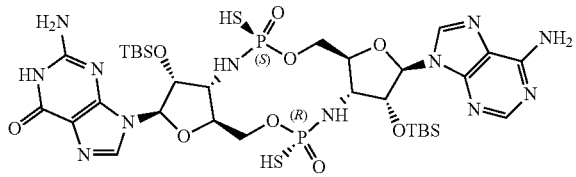

(8)

and h) the Compound 8 is subsequently deprotected to afford Compound I.

2. The process according to claim 1, wherein step b) further comprises a base selected from imidazole, DBU, diisopropylethylamine, triazole, tetrazole, metal alkoxide bases, lithium diisopropylamide, sodium bis(trimethysiliyl)amide or other amide bases.

3. The process according to claim 2, wherein the base is imidazole.

4. The process according to claim 1, wherein step c) further comprises a solvent selected from THF, MeCN or DMF.

5. The process according to claim 4, wherein the solvent is THF.

6. The process according to claim 1, wherein step c) further comprises a base selected from lithium diisopropylamide, sodium bis(trimethysiliyl)amide, other amide bases, potassium t-butoxide, DBU or other alkoxide bases.

7. The process according to claim 6, wherein the base in step c) is sodium tert-pentoxide or sodium t-amylate.

8. The process according to claim 1, wherein the solvent in step d) is THF, 2-MeTHF, MeCN or DMF.

9. The process according to claim 8, wherein the solvent in step d) is 2-MeTHF.

10. The process according to claim 1, wherein the base in step d) is imidazole, DBU, triazole, tetrazole, diisopropylethylamine or other t-butoxides.

11. The process according to claim 10, wherein the base in step d) is imidazole.

12. The process according to claim 1, wherein the solvent in step f) is THF, MeCN, NMP or DMF or mixtures thereof.

13. The process according to claim 12, wherein the solvent in step f) is a mixture of THF and NMP.

14. The process according to claim 1, wherein the base in step f) is lithium diisopropylamide, potassium bis(trimethylsilyl)amide, other amide bases, potassium t-butoxide, DBU, other alkoxide bases, NaHMDS or other alkylsilylamines.

15. The process according to claim 14, wherein the base in step f) is lithium t-butoxide.

16. The process according to claim 1, wherein the base in step g) is methylamine, ammonium or other alkylamine bases.

17. The process according to claim 16, wherein the base in step g) is methylamine.

* * * * *